United States Patent
Richelsoph et al.

(10) Patent No.: US 6,652,887 B1
(45) Date of Patent: Nov. 25, 2003

(54) BONE GRAFT SUBSTITUTE COMPOSITION

(75) Inventors: Kelly Coupe Richelsoph, Memphis, TN (US); Leasa C. Miller, Covington, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

(21) Appl. No.: 10/179,533

(22) Filed: Jun. 24, 2002

(51) Int. Cl.$^7$ .............................................. A61K 35/32
(52) U.S. Cl. ........................ 424/549; 424/682; 424/696
(58) Field of Search .............................. 424/549, 682, 424/696

(56) References Cited

U.S. PATENT DOCUMENTS

| | | | |
|---|---|---|---|
| 3,813,312 A | * | 5/1974 | Kindade et al. ............... 156/39 |
| 4,430,760 A | | 2/1984 | Smestad |
| 4,568,536 A | | 2/1986 | Kronenthal et al. |
| 4,595,713 A | | 6/1986 | St. John |
| 4,596,574 A | | 6/1986 | Urist |
| 4,612,009 A | | 9/1986 | Drobnik et al. |
| 4,619,655 A | | 10/1986 | Hanker et al. |
| 4,650,665 A | | 3/1987 | Kronenthal et al. |
| 4,681,763 A | | 7/1987 | Nathanson et al. |
| 4,820,306 A | | 4/1989 | Gorman et al. |
| 4,880,660 A | | 11/1989 | Aasen et al. |
| 4,882,149 A | | 11/1989 | Spector |
| 4,892,734 A | | 1/1990 | Leonard |
| 4,975,526 A | | 12/1990 | Kuberasampath et al. |
| 4,994,030 A | | 2/1991 | Glowczewskie, Jr. et al. |
| 5,061,286 A | | 10/1991 | Lyle |
| 5,073,373 A | | 12/1991 | O'Leary et al. |
| 5,147,403 A | | 9/1992 | Gitelis |
| 5,162,114 A | | 11/1992 | Kuberasampath et al. |
| 5,219,897 A | | 6/1993 | Murray |
| 5,236,456 A | | 8/1993 | O'Leary et al. |
| 5,236,971 A | | 8/1993 | Murray |
| 5,264,214 A | | 11/1993 | Rhee et al. |
| 5,284,655 A | | 2/1994 | Bogdansky et al. |
| 5,290,558 A | | 3/1994 | O'Leary et al. |
| 5,298,254 A | | 3/1994 | Prewett et al. |
| 5,306,304 A | | 4/1994 | Gendler |
| 5,314,476 A | | 5/1994 | Prewett et al. |
| 5,320,844 A | | 6/1994 | Liu |
| 5,336,699 A | | 8/1994 | Cooke et al. |
| 5,356,629 A | | 10/1994 | Sander et al. |
| 5,366,507 A | | 11/1994 | Sottosanti |
| 5,385,887 A | | 1/1995 | Yim et al. |
| 5,405,390 A | | 4/1995 | O'Leary et al. |
| 5,417,975 A | | 5/1995 | Lussi et al. |
| 5,425,769 A | | 6/1995 | Snyders, Jr. |
| 5,439,684 A | | 8/1995 | Prewett et al. |
| 5,462,722 A | | 10/1995 | Liu et al. |
| 5,482,551 A | | 1/1996 | Morris et al. |
| 5,484,601 A | | 1/1996 | O'Leary et al. |
| 5,507,813 A | | 4/1996 | Dowd et al. |
| 5,510,396 A | | 4/1996 | Prewett et al. |
| 5,512,610 A | | 4/1996 | Lin |
| 5,531,791 A | | 7/1996 | Wolfinbarger, Jr. |
| 5,569,308 A | | 10/1996 | Sottosanti |
| 5,573,771 A | | 11/1996 | Geistlich et al. |
| 5,578,662 A | | 11/1996 | Bennett et al. |
| 5,614,206 A | | 3/1997 | Randolph et al. |
| 5,618,549 A | | 4/1997 | Patat et al. |
| 5,676,146 A | | 10/1997 | Scarborough |
| 5,681,873 A | | 10/1997 | Norton et al. |
| 5,697,981 A | | 12/1997 | Ison et al. |
| 5,700,289 A | | 12/1997 | Breitbart et al. |
| 5,707,962 A | | 1/1998 | Chen et al. |
| 5,727,945 A | | 3/1998 | Dannenbaum |
| 5,756,127 A | | 5/1998 | Grisoni et al. |
| 5,763,416 A | | 6/1998 | Bonadio et al. |
| 5,766,618 A | | 6/1998 | Laurencin et al. |
| 5,769,897 A | | 6/1998 | Harle |
| 5,788,976 A | | 8/1998 | Bradford |
| 5,807,567 A | | 9/1998 | Randolph et al. |
| 5,824,087 A | | 10/1998 | Aspden et al. |
| 5,830,493 A | | 11/1998 | Yokota et al. |
| 5,861,445 A | | 1/1999 | Xu et al. |
| 5,899,939 A | | 5/1999 | Boyce et al. |
| 5,910,315 A | | 6/1999 | Stevenson et al. |
| 5,948,426 A | | 9/1999 | Jefferies |
| 5,948,428 A | | 9/1999 | Lee et al. |
| 5,964,805 A | | 10/1999 | Stone |
| 5,972,368 A | | 10/1999 | McKay |
| 5,981,828 A | | 11/1999 | Nelson et al. |
| 6,030,635 A | | 2/2000 | Gertzman et al. |
| 6,030,636 A | | 2/2000 | Randolph et al. |
| 6,037,519 A | | 3/2000 | McKay |
| 6,051,247 A | | 4/2000 | Hench et al. |
| 6,056,970 A | | 5/2000 | Greenawalt et al. |
| 6,071,530 A | | 6/2000 | Polson et al. |
| 6,083,522 A | | 7/2000 | Chu et al. |
| 6,118,043 A | | 9/2000 | Nies et al. |
| 6,224,635 B1 | | 5/2001 | Ricci et al. |
| 6,340,477 B1 | * | 1/2002 | Anderson ................... 424/488 |
| 2002/0016636 A1 | | 2/2002 | Ricci et al. |

FOREIGN PATENT DOCUMENTS

| | | |
|---|---|---|
| WO | WO 96/39203 | 12/1996 |
| WO | WO 98/40113 | 9/1998 |

OTHER PUBLICATIONS

Advances in Biomaterials for Bone Regeneration, Orthopedics, vol. 26, No. 5/Supplement, May 2003.

Randal R. Betz, M.D., "Limitations of Autograft and Allograft: New Synthetic Solutions", Orthopedics, vol. 25, No. 5, Supplement May 2002.

(List continued on next page.)

Primary Examiner—Jean C. Witz
(74) Attorney, Agent, or Firm—Fish & Richardson P.C.

(57) ABSTRACT

A composition includes calcium sulfate hemihydrate, an accelerant material, e.g., calcium sulfate dihydrate, a plasticizing material, a mixing solution, and demineralized bone matrix having a moisture content of between about 10 and about 30 weight percent.

29 Claims, No Drawings

OTHER PUBLICATIONS

"Bone Graft Substitutes Safe, Effective", AMA Science News Media Briefings, Dec. 6, 2001.

Turner et al., "Radiographic and Histologic Assessment of Calcium Sulfate in Experimental Animal Models and Clinical use as a Resorbable Bone–Graft Substitute, A Bone–Graft Expander, and a Method for Local Antibiotic Delivery", The Journal of Bone and Joint Surgery, Incorporated, vol. 83–A, Supp. 2, Part 1, 2001.

Greenwald et al., "Bone–Graft Substitutes: Facts, Fictions, and Applications", The Journal of Bone & Joint Surgery, JBJS Org., vol. 83–A, Supplement 2, Part 2, 2001.

Evelyn B. Kelly, Ph.D., "New Frontiers in Bone Grafting", Orthopaedic Technology Review, vol. 2, No. 9, Oct. 2000.

Adkisson et al., "Rapid Quantitative Bioassay of Osteoinduction", Journal of Orthopaedic Research, 18:503–511, 2000.

Hanker et al., "Setting of Composite Hydroxylaptie/Plaster Implants with Blood for Bone Reconstruction," Proceedings of the $44^{th}$ Annual Meeting of the Electron Microscopy Society of America, 1986.

Biomaterials Tutorial, www.btec.cmu.edu/tutorial/biomaterials/biomaterials.htm, Undated.

* cited by examiner

BONE GRAFT SUBSTITUTE COMPOSITION

TECHNICAL FIELD

The invention relates to bone graft substitute compositions.

BACKGROUND

Compositions containing calcium sulfate can be used as filler for voids and/or defects defined by bone. In some embodiments, the compositions can promote bone growth.

SUMMARY

The invention relates to bone graft substitute compositions.

In one aspect, the invention features a composition including calcium sulfate hemihydrate, a first material that accelerates the calcium sulfate hemihydrate to calcium sulfate dihydrate, a plasticizing material, and demineralized bone matrix having a moisture content of between about 10 and about 30 weight percent.

Embodiments may include one or more of the following features. The calcium sulfate dihydrate is stabilized with sucrose. The plasticizing material includes hydroxypropylmethylcellulose. The plasticizing material includes a material selected from a group consisting of sodium carboxymethylcellulose, methylcellulose, hydroxypropylcellulose, ethylcellulose, hydroxyethylcellulose or cellulose acetate butyrate, glycerol, vinyl alcohols, stearic acid, and hyaluronic acid. The first material includes calcium sulfate dihydrate. The composition further includes a mixing solution, such as water. The mixing solution includes a material selected from a group consisting of sodium chloride, phosphate buffered saline, potassium chloride, sodium sulfate, potassium sulfate, EDTA, ammonium sulfate, ammonium acetate, and sodium acetate. The demineralized bone matrix has a moisture content of between about 10 and about 20 weight percent, e.g., between about 10 and about 15 weight percent.

In certain embodiments, the composition includes 100 parts of calcium sulfate hemihydrate, about 0.5 to about 5 parts of the calcium sulfate dihydrate, about 0.5 to about 5 parts of the plasticizing material, about 40 to about 60 parts of the mixing solution, and about 10 to about 30 parts of the demineralized bone matrix. The composition may include 100 parts of calcium sulfate hemihydrate, about 1 to about 5, e.g., about 4.8, parts of the calcium sulfate dihydrate, about 1 to about 3 parts of the plasticizing material, about 45 to about 55 parts of the mixing solution, and about 15 to about 25 parts of the demineralized bone matrix.

In another aspect, the invention features a method of making a bone graft substitute composition. The method includes providing a mixture having calcium sulfate hemihydrate, calcium sulfate dihydrate, a plasticizing material, and demineralized bone matrix having a moisture content between about 10 and about 30 weight percent; and contacting a mixing solution with the mixture. In some embodiments, the plasticizing material includes hydroxypropylmethylcellulose, the demineralized bone matrix has a moisture content between about 10 and about 20 weight percent, and/or the mixing solution includes water.

In another aspect, the invention features a kit including a mixture having calcium sulfate hemihydrate, calcium sulfate dihydrate, a plasticizing material, and demineralized bone matrix having a moisture content between about 10 and about 30 weight percent; and a mixing solution unblended with the mixture. In some embodiments, the plasticizing material includes hydroxypropylmethylcellulose, the demineralized bone matrix has a moisture content between about 10 and about 20 weight percent, and/or the mixing solution includes water.

Embodiments may have one or more of the following advantages. The composition is capable of setting or hardening in a relatively short time. In embodiments, the composition can harden in about 5–10 minutes. The composition is capable of setting or hardening in vivo or ex vivo. The composition can promote bone growth.

Other aspects, features, and advantages of the invention will be apparent from the description of the preferred embodiments thereof and from the claims.

DETAILED DESCRIPTION

A bone graft substitute composition includes calcium sulfate hemihydrate ($CaSO_4 \cdot \frac{1}{2} H_2O$); demineralized bone matrix; a material that accelerates hardening of the composition ("an accelerant"); a plasticizing material; and a mixing solution. In some embodiments, the calcium sulfate, the demineralized bone matrix, the plasticizing material, and the accelerant are provided as a mixture of powders to which the mixing solution is added to form the composition. The composition can be delivered to a target site (e.g., a void or a defect) by injecting the composition through a syringe, and/or by forming a paste or a putty of the composition and applying the composition by hand (e.g., using fingers). The composition can harden ex vivo or in vivo, e.g., to a hardness sufficient to support orthopedic hardware.

Without wishing to be bound by theory, it is believed that during use, e.g., after mixing the mixture of powders with the mixing solution, the calcium sulfate hemihydrate is converted, e.g., changes crystalline form, into calcium sulfate dihydrate ($CaSO_4 \cdot 2H_2O$), which hardens the composition. Calcium sulfate dihydrate is capable of being sorbed by the body. For purposes of describing the concentrations of materials in the bone graft substitute composition, the composition includes 100 parts of calcium sulfate, e.g., calcium sulfate hemihydrate. Methods of making a calcium sulfate hemihydrate are described in U.S. Pat. Nos. 5,614,206, 5,807,567, and 6,030,636, each of which is hereby incorporated by reference in its entirety.

The demineralized bone matrix is believed to enhance bone growth. The demineralized bone matrix, e.g., freeze-dried or air-dried, preferably includes between about 10 and about 30 weight percent (e.g., between about 10–20 weight percent, between about 10–15 weight percent, or between about 10–12 weight percent) of moisture, e.g., water. In some embodiments, the demineralized bone matrix includes greater than or equal to about 10, 12, 14, 16, 18, 20, 22, 24, 26, or 28 weight percent of moisture; and/or less than or equal to about 30, 28, 26, 24, 22, 20, 18, 16, 14, or 12 weight percent of moisture.

In certain embodiments, the demineralized bone matrix, along with other materials in the substitute composition, are packaged in a kit and subjected to sterilization, e.g., electron beam sterilization, prior to being used. Without wishing to be bound by theory, it is believed that if the demineralized bone matrix includes less than the disclosed amount of moisture, the sterilization process can affect (e.g., increase) the "free" protein in the bone matrix and affect (e.g., inhibit) the setting or hardening of the mixed composition. If the demineralized bone matrix includes the disclosed amount of moisture, the protein level in the bone matrix may be unaffected by the sterilization process. For example, it is believed that water can interact with electrons in an electron beam sterilization process, thereby reducing (e.g., preventing) the interaction between proteins in the bone matrix and electrons in the beam.

The moisture level of the demineralized bone matrix can be controlled in a number of ways. For example, the bone matrix can be air-dried rather than freeze dried. Air dried demineralized bone matrix can include greater than about 10 weight percent of moisture, while in certain circumstances, freeze dried demineralized bone matrix can include less than about 6 weight percent of moisture. In addition or alternatively, the demineralized bone matrix can be packaged separately from the other powdered ingredients (e.g., accelerant or plasticizing material), and a predetermined amount of water (e.g., about 10–20%) can be added to the bone matrix prior to the sterilization process. In addition or alternatively, a source of moisture, such as a water-sorbed sponge, can be packaged with the demineralized bone matrix. The moisture level of the demineralized bone matrix can also be increased by placing demineralized bone matrix in a humidity chamber. Demineralized bone matrix is available, e.g., from Allosource (Denver, Colo.) or DCI (Nashville, Tenn.).

In some embodiments, the demineralized bone matrix has a particle size of about 125–850 microns, e.g., about 125–710 microns. The particle size can be greater than or equal to about about 125, 150, 200, 250, 300, 350, 400, 450, 500, 550, 600, 650, 700, 750, or 800 microns; and/or less than or equal to about about 850, 800, 750, 700, 650, 600, 550, 500, 450, 400, 350, 300, 250, 200, or 150 microns. The calcium content in the demineralized bone matrix can be about less than two percent.

For 100 parts of calcium sulfate (e.g., $CaSO_4 \cdot \frac{1}{2}H_2O$), the composition includes between about 10 and about 30 parts of demineralized bone matrix, such as between about 15 and about 25 parts, or between about 19 and about 21 parts, or about 20 parts. In embodiments, the composition may include greater than or equal to about 10, 12, 14, 16, 18, 20, 22, 24, 26, or 28 parts of demineralized bone matrix; and/or less than or equal to about 30, 28, 26, 24, 22, 20, 18, 16, 14, or 12 parts of demineralized bone matrix.

Without wishing to be bound by theory, the accelerant is believed to enhance, e.g., accelerate, the conversion of calcium sulfate hemihydrate to calcium sulfate dihydrate. In particular, it is believed that particles of the accelerant act as crystallization nucleation sites for the conversion of calcium sulfate hemihydrate to calcium sulfate dihydrate. Examples of accelerants include calcium sulfate dihydrate, potassium sulfate, or sodium sulfate. Other examples include ionic salts. A preferred accelerant is calcium sulfate dihydrate crystals (available from U.S. Gypsum) coated with sucrose (available from VWR Scientific Products). A process of stabilizing the dihydrate crystals by coating with sucrose is described in U.S. Pat. No. 3,573,947, hereby incorporated by reference in its entirety.

For 100 parts of calcium sulfate (e.g., $CaSO_4 \cdot \frac{1}{2}H_2O$), the composition includes between about 0.5 and about 5 parts of the accelerant, such as about 4.8 parts, or between about 1 and about 4 parts, or between about 2.5 and about 3.5 parts, or about 3 parts. The composition may include greater than or equal to about 0.5, 1, 1.5, 2, 2.5, 3, 3.5, 4, or 4.5 parts of the accelerant; and/or less than or equal to about 5, 4.5, 4, 3.5, 3, 2.5, 2, 1.5, or 1 parts of the accelerant. Mixtures of two or more accelerants can be used.

The plasticizing material is believed to provide the bone graft substitute composition with a consistency that helps the composition to form into a paste or putty, or to flow, e.g., to be injectable. Examples of plasticizing materials include cellulose derivatives, such as sodium carboxymethylcellulose, methylcellulose (MC), hydroxypropylmethylcellulose (HPMC), hydroxypropylcellulose (HPC), ethylcellulose (EC), hydroxyethylcellulose or cellulose acetate butyrate. Other examples of plasticizing material include high molecular weight alcohols including glycerol and vinyl alcohols, stearic acid, and hyaluronic acid.

For 100 parts of calcium sulfate (e.g., $CaSO_4 \cdot \frac{1}{2}H_2O$), the composition includes between about 0.5 and about 5 parts of the plasticizing material, such as between about 1 and about 3 parts, or between about 1.5 and about 2.5 parts, or about 2 parts. The composition may include greater than or equal to about 0.5, 1, 1.5, 2, 2.5, 3, 3.5, 4, or 4.5 parts of the plasticizing material; and/or less than or equal to about 5, 4.5, 4, 3.5, 3, 2.5, 2, 1.5, or 1 parts of the plasticizing material. Mixtures of two or more plasticizing materials can be used.

The mixing solution is generally selected to provide the composition with a desired consistency and hardening time. Examples of a mixing solution include water, e.g., sterile water, solutions containing inorganic salts, or cationic surface active agents including sodium chloride, saline, e.g., phosphate buffered saline, potassium chloride, sodium sulfate, potassium sulfate, EDTA, ammonium sulfate, ammonium acetate, and sodium acetate. A specific example of a mixing solution is 0.9% NaCl saline solution (available from Baxter).

The concentration of mixing solution in the substitute composition varies and can be a function of, for example, the source (e.g., tissue bank) of the demineralized bone matrix, and/or the desired consistency of the composition. Also, the amount of mixing solution added to the mixture of powders can affect the time the composition takes to set, i.e., the set time. Increasing the amount of mixing solution can increase the set time, and decreasing the amount of mixing solution added to the mixture of powders can reduce the set time. For example, for a putty having HPMC, 2.6 grams of water provided a set time of about 10–15 minutes, while 4.0 grams of water provided a set time of about 60 minutes.

In some embodiments, for 100 parts of calcium sulfate (e.g., $CaSO_4 \cdot \frac{1}{2}H_2O$), the composition includes between about 40 and about 60 parts of the mixing solution, such as between about 45 and about 55 parts, or between about 49 and about 51 parts, or about 50 parts. The composition may include greater than or equal to about 40, 45, 50, or 55 parts of the mixing solution; and/or less than or equal to about 60, 55, 50, or 45 parts of the mixing solution. Mixtures of two or more mixing solutions can be used.

The mixing solution can further include, for example, bone marrow aspirate, platelet concentrate, blood, pharmaceutical additives in solution, or combinations of these materials. Examples of additives are medicaments or pesticides. Examples of medicaments are antibiotics, chemotherapeutic agents, growth factors, and analgesics. Examples of antibiotics are tetracycline hydrochloride, vancomycin, cephalosporins, and aminoglycocides such as tobramycin and gentamicin. Examples of chemotherapeutic agents are cis-platinum, ifosfamide, methotrexate, and doxorubicin hydrochloride (Adriamycin®). Examples of growth factors are transforming growth factor beta (TGF-Beta), bone morphogenic protein (BMP), basic fiberblast growth factor, platelet-derived growth factor, and other polypeptide growth factors. Examples of analgesics are anesthetics such as lidocaine hydrochloride (Xylocaine®), bipivacaine hydrochloride (Marcaine®), and non-steroidal anti-inflammatory drugs such as ketorolac tromethamine (Toradol®). Certain mixing solution and/or additives can affect, e.g., delay, the hardening properties of the composition.

The composition can be formed by providing the mixture of powders (e.g., calcium sulfate hemihydrate, demineralized bone matrix, HPMC, and calcium sulfate dihydrate) and contacting, e.g., mixing, the mixture with a mixing solution (e.g., NaCl saline) to form the composition. The composition may be a conforming material having a paste-like or putty-like consistency, e.g., like Plaster of Paris, that can be applied digitally. The material can be injected into a target site, for example, to fill into cracks or voids. In some embodiments, the composition is capable of setting to a hardness, e.g., about 4.3 MPa, in about 5–15 minutes, e.g., greater than 5, 7, 9, 11, or 13 minutes, and/or less than 15, 13, 11, 9, or 7 minutes.

The hardened composition can be used for intra-operative support of hardware, such as orthopedic hardware, e.g., bone plates, distal radius hardware, and hardware used for tibial plateau fractures.

The following examples are illustrative and not intended to be limiting.

EXAMPLE 1

A mixture of powders (4.17 grams) was formed having 2.3375 grams (56.055 wt %, 100 parts) of $CaSO_4 \cdot \frac{1}{2}H_2O$ (U.S. Gypsum), 0.1125 gram (2.698 wt %, 4.8 parts) of $CaSO_4 \cdot \frac{1}{2}H_2O$ (U.S. Gypsum), 0.05 gram (1.199 wt %, 2.1 parts) of HPMC (Hercules), and 0.48 gram (11.511 wt %, 20.5 parts) of demineralized bone matrix (DBM) having 13% moisture. The demineralized bone matrix was made by adding, prior to sterilization, about 10% by weight of water to a vial containing freeze dried DBM (Allosource) having about 3.19% moisture content. 1.19 gram (28.537 wt %, 50.9 parts) of water was added to the mixture of powders, and mixed together to form a composition having a putty-like consistency.

EXAMPLE 2

A mixture of powders was formed having 100 parts of $CaSO_4 \cdot \frac{1}{2}H_2O$ (U.S. Gypsum), 3.2 parts of $CaSO_4 \cdot \frac{1}{2}H_2O$ (U.S. Gypsum), 2.1 parts of HPMC (Hercules), and 20.3 parts of demineralized bone matrix (DBM) having 13% moisture. The demineralized bone matrix was made by adding, prior to sterilization, about 10% by weight of water to a vial containing freeze dried DBM (Allosource) having about 3.19% moisture content. About 50.2 parts of water was added to the mixture of powders, and mixed together to form a composition having a putty-like consistency.

After about four minutes, the composition hardened, e.g., to about 4 MPa.

Other Embodiments

In some embodiments, the composition further includes a bioactive agent. Examples of bioactive agents include demineralized bone matrix, growth factors, hyaluronic acid, bone morphogenic proteins, bone autograft, and bone marrow, etc. The composition may include sodium bicarbonate. For example, the composition may include 0.1–2% sodium bicarbonate by weight to provide a porous structure in the resultant composition.

Alternatively or in addition, the bone graft substitute composition may include one or more additive such as an antiviral agent, an antimicrobial agent, an antibiotic agent, an amino acid, a peptide, a vitamin, an inorganic element, a protein synthesis co-factor, a hormone, an endocrine tissue, a synthesizer, an enzyme, a polymer cell scaffolding agent with parenchymal cells, an angiogenic drug, a collagen lattice, an antigenic agent, a cytoskeletal agent, mesenchymal stem cells, a bone digester, an antitumor agent, an cellular attractant, fibronectin, a growth hormone, a cellular attachment agent, an immunosuppressant, a nucleic acid, a surface active agent, synthetically derived or naturally derived chips of minerals such as calcium phosphate, e.g., hydroxyapatite or tricalcium phosphate, or calcium carbonate, a penetration enhancer, allografts, e.g., a bone allograft, cancellous bone chip (an osteoconductive substrate), and chunks, shards, and/or pellets of calcium sulfate.

Other embodiments are within the claims.

What is claimed is:

1. A composition, comprising:
    calcium sulfate hemihydrate;
    a first material that accelerates the calcium sulfate hemihydrate to calcium sulfate dihydrate;
    a plasticizing material; and
    demineralized bone matrix having a moisture content of between about 10 and about 30 weight percent.

2. The composition of claim 1, wherein the calcium sulfate dihydrate is stabilized with sucrose.

3. The composition of claim 1, wherein the first material comprises calcium sulfate dihydrate.

4. The composition of claim 1, wherein the plasticizing material comprises hydroxypropylmethylcellulose.

5. The composition of claim 1, wherein the plasticizing material includes a material selected from a group consisting of sodium carboxymethylcellulose, methylcellulose, hydroxypropylcellulose, ethylcellulose, hydroxyethylcellulose or cellulose acetate butyrate, glycerol, vinyl alcohols, stearic acid, and hyaluronic acid.

6. The composition of claim 1, further comprising a mixing solution.

7. The composition of claim 6, wherein the mixing solution comprises water.

8. The composition of claim 6, wherein the mixing solution includes a material selected from a group consisting of sodium chloride, phosphate buffered saline, potassium chloride, sodium sulfate, potassium sulfate, EDTA, ammonium sulfate, ammonium acetate, and sodium acetate.

9. The composition of claim 1, wherein the demineralized bone matrix has a moisture content of between about 10 and about 20 weight percent.

10. The composition of claim 1, wherein the demineralized bone matrix has a moisture content of between about 10 and about 15 weight percent.

11. The composition of claim 1, wherein the demineralized bone matrix has a moisture content of between about 10 and about 12 weight percent.

12. The composition of claim 1, comprising
    100 parts of calcium sulfate hemihydrate;
    about 0.5 to about 5 parts of the first material;
    about 0.5 to about 5 parts of the plasticizing material; and
    about 10 to about 30 parts of the demineralized bone matrix.

13. The composition of claim 12, wherein the plasticizing material comprises hydroxypropylmethylcellulose.

14. The composition of claim 12, further comprising about 40 to about 60 parts of a mixing solution.

15. The composition of claim 14, wherein the mixing solution comprises water.

16. The composition of claim 14, wherein the first material comprises calcium sulfate dihydrate.

17. The composition of claim 1, comprising 100 parts of calcium sulfate hemihydrate;

about 1 to about 4 parts of the first material;

about 1 to about 3 parts of the plasticizing material; and about 15 to about 25 parts of the demineralized bone matrix.

18. The composition of claim 17, wherein the first material comprises calcium sulfate dihydrate.

19. The composition of claim 17, wherein the plasticizing material comprises hydroxypropylmethylcellulose.

20. The composition of claim 17, further comprising about 45 to about 55 parts of a mixing solution.

21. The composition of claim 20, wherein the mixing solution comprises water.

22. A method of making a bone graft substitute composition, the method comprising:

contacting a mixture comprising calcium sulfate hemihydrate, calcium sulfate dihydrate, a plasticizing material, and demineralized bone matrix having a moisture content between about 10 and about 30 weight percent, with a mixing solution.

23. The method of claim 22, wherein the plasticizing material comprises hydroxypropylmethylcellulose.

24. The method of claim 22, wherein the demineralized bone has a moisture content between about 10 and about 20 weight percent.

25. The method of claim 22, wherein the mixing solution comprises water.

26. A kit, comprising:

a mixture comprising:

calcium sulfate hemihydrate;

calcium sulfate dihydrate;

a plasticizing material; and demineralized bone matrix having a moisture content between about 10 and about 30 weight percent; and a mixing solution unblended with the mixture.

27. The kit of claim 26, wherein the plasticizing material comprises hydroxypropylmethylcellulose.

28. The kit of claim 26, wherein the demineralized bone matrix has a moisture content between about 10 and about 20 weight percent.

29. The kit of claim 26, wherein the mixing solution comprises water.

* * * * *